(12) United States Patent
Jardien et al.

(10) Patent No.: US 7,345,192 B2
(45) Date of Patent: Mar. 18, 2008

(54) REDUCTION OF HAIR GROWTH

(75) Inventors: Anwar Jardien, Brookline, MA (US); Roman Rariy, Allston, MA (US); Gurpreet S. Ahluwalia, Newton, MA (US); Douglas Shander, Acton, MA (US)

(73) Assignee: The Gillette Company, Boston, MA (US)

( * ) Notice: Subject to any disclaimer, the term of this patent is extended or adjusted under 35 U.S.C. 154(b) by 0 days.

(21) Appl. No.: 11/272,250

(22) Filed: Nov. 10, 2005

(65) Prior Publication Data

US 2006/0067903 A1 Mar. 30, 2006

(51) Int. Cl.
C07C 220/00 (2006.01)
C07C 53/15 (2006.01)
A01N 33/18 (2006.01)

(52) U.S. Cl. .................. 560/169; 560/206; 560/226; 514/740

(58) Field of Classification Search ............... 560/155, 560/172, 226, 227; 564/192, 193, 197, 209; 514/506, 529, 546, 550, 553, 613, 625, 626, 514/628
See application file for complete search history.

(56) References Cited

U.S. PATENT DOCUMENTS

| | | | |
|---|---|---|---|
| 3,426,137 A | 2/1969 | Philpitt et al. | |
| 4,039,669 A | 8/1977 | Beyler et al. | |
| 4,139,638 A | 2/1979 | Neri et al. | |
| 4,161,540 A | 7/1979 | Neri et al. | |
| 4,191,775 A | 3/1980 | Glen | |
| 4,269,831 A | 5/1981 | Ferrari et al. | |
| 4,370,315 A | 1/1983 | Greff et al. | |
| 4,508,714 A | 4/1985 | Cecic et al. | |
| 4,517,175 A | 5/1985 | Iwabuchi et al. | |
| 4,720,489 A * | 1/1988 | Shander | 514/71 |
| 4,885,289 A | 12/1989 | Breuer et al. | |
| 4,935,231 A | 6/1990 | Pigiet | |
| 5,095,007 A | 3/1992 | Ahluwalia | |
| 5,096,911 A | 3/1992 | Ahluwalia et al. | |
| 5,132,293 A | 7/1992 | Shander et al. | |
| 5,143,925 A | 9/1992 | Shander et al. | |
| 5,189,212 A | 2/1993 | Ruenitz | |
| 5,271,942 A | 12/1993 | Heverhagen | |
| 5,300,284 A | 4/1994 | Wiechers et al. | |
| 5,328,686 A | 7/1994 | Shander et al. | |
| 5,362,748 A | 11/1994 | Schwen et al. | |
| 5,364,885 A | 11/1994 | Ahluwalia et al. | |
| 5,411,991 A | 5/1995 | Shander et al. | |
| 5,444,090 A | 8/1995 | Ahluwalia | |

(Continued)

FOREIGN PATENT DOCUMENTS

BE 881 208 6/1980

(Continued)

OTHER PUBLICATIONS

Silverman, The Organic Chemistry of Drug Design and Drug Action (1992) pp. 352-357.*

(Continued)

*Primary Examiner*—Karl Puttlitz
(74) *Attorney, Agent, or Firm*—Fish & Richardson P.C.

(57) ABSTRACT

Compositions including a conjugate of α-difluoromethylornithine can be applied topically to reduce hair growth.

4 Claims, 1 Drawing Sheet

U.S. PATENT DOCUMENTS

| | | | |
|---|---|---|---|
| 5,455,234 | A | 10/1995 | Ahluwalia et al. |
| 5,468,476 | A | 11/1995 | Ahluwalia et al. |
| 5,474,763 | A | 12/1995 | Shander et al. |
| 5,554,608 | A | 9/1996 | Ahluwalia et al. |
| 5,645,825 | A | 7/1997 | Hillebrand et al. |
| 5,648,394 | A | 7/1997 | Boxall et al. |
| 5,652,273 | A | 7/1997 | Henry et al. |
| 5,674,477 | A | 10/1997 | Ahluwalia |
| 5,728,736 | A | 3/1998 | Shander et al. |
| 5,776,442 | A | 7/1998 | Ahluwalia |
| 5,824,665 | A | 10/1998 | Henry et al. |
| 5,840,752 | A | 11/1998 | Henry et al. |
| 5,908,867 | A | 6/1999 | Henry et al. |
| 5,939,458 | A | 8/1999 | Henry et al. |
| 5,958,946 | A | 9/1999 | Styczynski et al. |
| 5,962,466 | A | 10/1999 | Styczynski et al. |
| 6,020,006 | A | 2/2000 | Styczynski et al. |
| 6,037,326 | A | 3/2000 | Styczynski et al. |
| 6,060,471 | A | 5/2000 | Styczynski et al. |
| 6,093,748 | A | 7/2000 | Ahluwalia et al. |
| 6,121,269 | A | 9/2000 | Henry et al. |
| 6,218,435 | B1 | 4/2001 | Henry et al. |
| 6,235,737 | B1 | 5/2001 | Styczynski et al. |
| 6,239,170 | B1 | 5/2001 | Ahluwalia et al. |
| 6,248,751 | B1 | 6/2001 | Ahluwalia et al. |
| 6,284,234 | B1 | 9/2001 | Niemiec et al. |
| 6,299,865 | B1 | 10/2001 | Styczynski et al. |
| 2003/0053973 | A1 | 3/2003 | Chou et al. |

FOREIGN PATENT DOCUMENTS

| | | |
|---|---|---|
| EP | 0 532 219 A2 | 9/1992 |
| GB | 1 458 349 | 12/1976 |
| WO | WO 98/02134 | 1/1998 |
| WO | WO 98/14188 | 4/1998 |
| WO | WO 01/68076 | 9/2001 |
| WO | WO 02/086138 | 10/2002 |
| WO | WO 03/013496 | 2/2003 |
| WO | WO 03/020209 | 3/2003 |

OTHER PUBLICATIONS

Goodman and Gilman's "The Pharmacological Basis of Therapeutics", 8th ed. (1990) pp. 13-18.*

Montagna et al., Journal of Anatomy, v. 89, 1955 pp. 425-429.*

Roberts et al.,, "Skin Transport", Dermatological and Transdermal Formulation. Drugs and the Pharmaceutical Sciences, Marcel Dekker US, 119, 89-195, 2002.

Khazaei et al., "A novel synthesis and characterization of poly[4-imino(N-4-ethylbenzoate)benzene p-styrenesulphonate] and the investigation on polymer ability for drug release", Iranian Polymer Journal, 10(1), 59-65, 2001.

Malhotra et al:, "Percutaneous Absorption and Pharmacokinetics of Eflornithine HCI 13.9% Cream in Women with Unwanted Facial Hair", J. Clin. Pharmacol. 41, 972-978, 2001.

Beisson et al., "Use of the Tape Stripping Technique for Directly Quantifying Esterase Activities in Human Stratum", Corneum. Anal. Biochem, 290, 179-185, 2001.

Shander et.al., "Clinical dose range studies with topical application of the ornithine decarboxylase inhibitor eflornithline HCI (a-difluoromethyl-dl-ornithine; DFMO) in women with facial hirsutism", Abstract # P 123, American Academy of Dermatology 59th Annual Meeting, 2001.

Schrode et,al., "Randomized, double-blind, vehicle-controlled safety and efficacy evaluation of eflornithine 15% cream in the treatment of women with excessive facial hair", Abstract # P291, Americal Academy of Dermatology 58th Annual Meeting, 2000.

Huber, et,al., "Use of a video imaging system to obtain hair measurement data in controlled clinical trials evaluating the safety and efficacy of eflornithine 15% cream in the treatment of excessive facial hair in women", Abstract # P292, Americal Academy of Dermatology 58th Annual Meeting, 2000.

Huber, "Outcome of a quality of life assessment used in clinical trials for hirsute women treated with topical eflornithine 15% cream", Abstract # P293, Americal Academy of Dermatology 58th Annual Meeting, 2000.

Botchkatev et al., "A New Role for Neurotrophin-3", *American Journal of Pathology*, vol. 153, pp. 785-799, 1998.

Botchkarev et al., "Neurotrophin-3 Involvement in the Regulation of Hair Follicle Morphogenesis", *The Journal of Investigative Dermatology*, vol. 111, No. 2, pp. 279-285, 1998.

Hoffman et al., "Interleukin-1 β-Induced Inhibition of Hair Growth In Vitro Is Mediated by Cyclic AMP", *The Journal of Investigative Dermatology*, vol. 108, pp. 40-42, 1997.

Kouzuki et al., "Precutaneous absorption of amino acids. Part 2. Drug Delivery System", 11(5), 329-335, 1996.

Messenger, Andrew G., "The Control of Hair Growth: An Overview", *The Journal of Investigative Dermatology*, vol. 101, No. 1, pp. 4s-9s, 1993.

Weinberg et al., "Reconstitution of Hair Follicle Development In Vitro: Determination of Follicle Formation, Hair Growth, and Hair Quality by Dermal Cells", *The Journal of Investigative Dermatology*, vol. 100, pp. 229-236, 1993.

McCann, et al., "Ornithine Decarboxylase as an Enzyme Target for Therapy", Pharmac. Ther. 54: 195-215, 1992.

Ebling, F. John G., "The Biology of Hair", *Dermatologic Clinics*, vol. 5, No. 3, pp. 467-481, 1987.

Danzin et al., "Absence of stereospecificity in the suicide inhibition of ornithine decarboxylase", In Biochemistry of Vitamin B6, pp. 333-336, 1987.

Hattori et al., "Biochemical Analysis of Hair Growth From the Aspects of Aging and Enzyme Activities", *The Journal of Dermatology*, vol. 10, pp. 45-54, 1983.

Metcalf et al., "Catalytic Irreversible Inhibition of Mammalian Ornithine Decarboxylase (E.C.4.1.1.17) by Substrate and Product", Analogues. J. of the American Chemical Society. 100:2551-2553, 1978.

Adachi et al., "Human Hair Follicles: Metabolism and Control Mechanisms", *Journal of the Society of Cosmetic Chemists*, vol. 21, No. 13, pp. 901-924, 1970.

Sato, Yoshio, "The Hair Cycle and Its Control Mechanism", pp. 3-13, 1976.

Bey et.al. "Direct Synthesis of a-Halogenomethyl-a-amino acids from the parent a-amino acids", J. Org. Chem., 44: 2732-2742, 1979.

\* cited by examiner

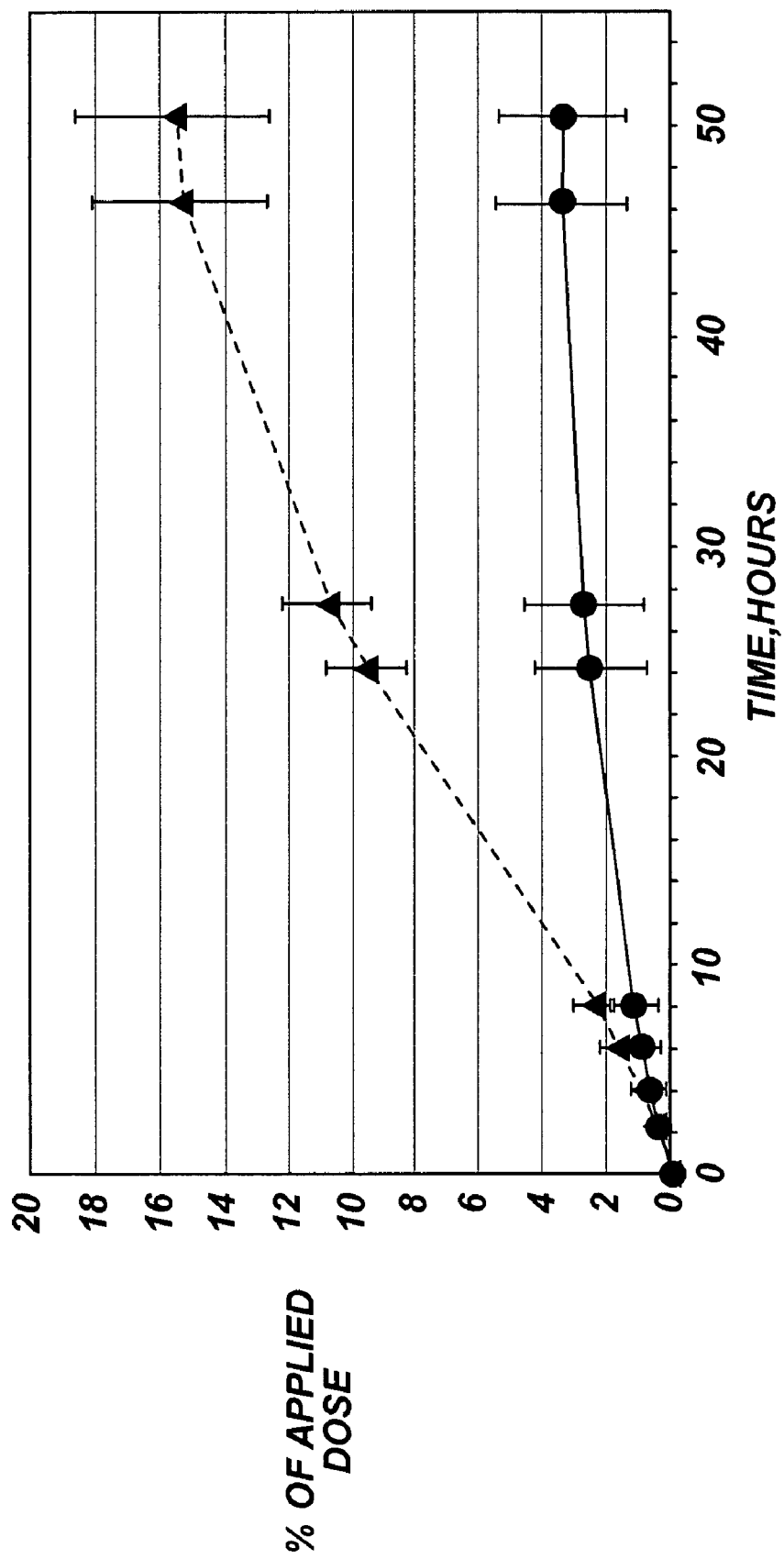

REDUCTION OF HAIR GROWTH

CLAIM OF PRIORITY

This application claims priority under 35 U.S.C. § 120 to U.S. patent application Ser. No. 10/397,132, filed on Mar. 26, 2003, the entire contents of which are hereby incorporated by reference.

BACKGROUND

The invention relates to reducing hair growth in mammals, particularly for cosmetic purposes.

A main function of mammalian hair is to provide environmental protection. However, that function has largely been lost in humans, in whom hair is kept or removed from various parts of the body essentially for cosmetic reasons. For example, it is generally preferred to have hair on the scalp but not on the face.

Various procedures have been employed to remove unwanted hair, including shaving, electrolysis, depilatory creams or lotions, waxing, plucking, and therapeutic antiandrogens. These conventional procedures generally have drawbacks associated with them. Shaving, for instance, can cause nicks and cuts, and can leave a perception of an increase in the rate of hair regrowth. Shaving also can leave an undesirable stubble. Electrolysis, on the other hand, can keep a treated area free of hair for prolonged periods of time, but can be expensive, painful, and sometimes leaves scarring. Depilatory creams, though very effective, typically are not recommended for frequent use due to their high irritancy potential. Waxing and plucking can cause pain, discomfort, and poor removal of short hair. Finally, antiandrogens—which have been used to treat female hirsutism—can have unwanted side effects.

It has previously been disclosed that the rate and character of hair growth can be altered by applying to the skin inhibitors of certain enzymes. These inhibitors include inhibitors of 5-alpha reductase, ornithine decarboxylase, S-adenosylmethionine decarboxylase, gamma-glutamyl transpeptidase, and transglutaminase. See, for example, Breuer et al., U.S. Pat. No. 4,885,289; Shander, U.S. Pat. No. 4,720,489; Ahluwalia, U.S. Pat. No. 5,095,007; Ahluwalia et al., U.S. Pat. No. 5,096,911; and Shander et al., U.S. Pat. No. 5,132,293.

α-Difluoromethylornithine (DFMO) is an inhibitor of ornithine decarboxylase (ODC). A skin preparation containing DFMO (sold under the name Vaniqa®, has been approved by the Food and Drug Administration (FDA) for the treatment of unwanted facial hair growth in women. Its topical administration in a cream based vehicle has been shown to reduce the rate of facial hair growth in women. Vaniqa® facial cream includes a racemic mixture of the "D-" and "L-" enantiomers of DFMO (i.e., D,L-DFMO) in the monohydrochloride form at a concentration of 13.9% by weight active (15%, as monohydrochloride monohydrate). The recommended treatment regimen for Vaniqa® is twice daily. The cream base vehicle in Vaniqa® is set out in Example 1 of U.S. Pat. No. 5,648,394, which is incorporated herein by reference.

It generally takes about eight weeks of continuous treatment before the hair growth-inhibiting efficacy of Vaniqa® cream becomes apparent. Vaniqa® cream has been shown to decrease hair growth an average of 47%. In one study, clinical successes were observed in 35% of women treated with Vaniqa® cream. These women exhibited marked improvement or complete clearance of their condition as judged by physicians scoring a decrease in visibility of facial hair and a decrease in skin darkening caused by hair. Another 35% of the women tested experienced some improvement in their condition. However, there were some women who exhibited little or no response to treatment.

Accordingly, although Vaniqa® cream is an effective product, it would be even more effective if it provided an earlier onset of hair growth inhibition (i.e., exhibited efficacy earlier than eight weeks) and/or exhibited an increased clinical success rate (i.e., exhibited efficacy in a greater percentage of users).

The stratum corneum serves as a barrier to the influx of pathogens and toxins and the efflux of physiological fluids. The envelopes of the cells in the stratum corneum consists mainly of polar lipids, such as ceramides, sterols and fatty acids while the cytoplasm of the stratum corneum cells remains polar and aqueous. Poor transdermal penetration of some drugs has, until now, frustrated attempts to deliver clinically significant doses by the topical route.

Molecules that are identical to each other in chemical structural formula and yet are not superimposable upon each other are enantiomers. In terms of their physiochemical properties enantiomers differ only in their ability to rotate the plane of plane-polarized light, and this property is frequently used in their designation. Those enantiomers that rotate plane-polarized light to the right are termed dextrorotatory, indicated by either a (+)- or d- or D-before the name of the compound; those that rotate light to the left are termed laevorotatory indicated by a (−)- or l- or L-prefix. A racemic mixture is indicated by either a (+)- or d,l- or D,L-prefix. By another convention (or nomenclature), the R,S or the sequence rule can be used to differentiate enantiomers based on their absolute configuration. Using this system the L-DFMO corresponds to the R-DFMO, and the D-DFMO corresponds to the S-DFMO. Enantiomers are physiochemically similar in that they have similar melting points, boiling points, relative solubility, and chemical reactivity in an achiral environment. A racemate is a composite of equal molar quantities of two enantiomeric species, often referred to as the DL-form. Individual enantiomers of chiral molecules may possess different pharmacological profiles, i.e., differences in pharmacokinetics, toxicity, efficacy, etc.

SUMMARY

The present invention provides a method (typically a cosmetic method) of reducing hair growth (for example, androgen-stimulated hair growth). The method generally includes applying to the skin, in an amount effective to reduce hair growth, a dermatologically acceptable composition including a conjugate of DFMO or a pharmaceutically acceptable salt thereof. Preferably, the conjugate is more lipophilic than DFMO and as a result penetrates the skin better than DFMO. In preferred embodiments, the conjugate cleaves (for example, enzymatically or hydrolytically) or dissociates after and/or during skin penetration to provide DFMO. The cleavage may or may not be stereospecific. When the cleavage is stereospecific, it preferably favors formation of L-DFMO over D-DFMO. In some embodiments, even if the conjugate is not converted to DFMO after and/or during skin penetration, the conjugate itself, or whatever the conjugate has been converted to after application to the skin, acts to reduce hair growth. Preferred conjugates include Schiff bases, esters, carbamates, carbamides, and esters of DFMO.

One preferred type of conjugate is a Schiff base of DFMO having the following structure:

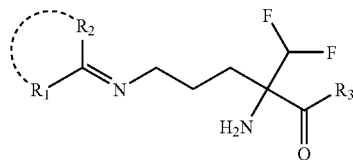

wherein $R_3$ is $XR_4$; X is O, N, or S; and each of $R_1$, $R_2$, and $R_4$, independently, is H, $C_{1-30}$ alkyl or $C_{2-30}$ aryl. $R_1$ and $R_2$ together may be part of a cyclic structure; this is represented in the above structure by the dashed line between $R_1$ and $R_2$. In some embodiments, each of $R_1$, $R_2$, and $R_4$, independently, is $C_{4-20}$ alkyl or $C_{5-20}$ aryl. In some preferred embodiments, $R_3$ is OH. The composition preferably includes a non-aqueous vehicle. The Schiff base preferably dissociates upon reaching an aqueous environment in the skin.

Another preferred type of conjugate has the following structure:

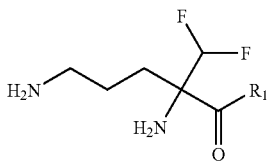

wherein $R_1$ is $XR_2$; X is O, N, or S; and $R_2$ is H, $C_{1-30}$ alkyl, or $C_{2-30}$ aryl; except that, when X is O, $R_2$ is not H. In some preferred embodiments, X is O and the compound is an ester of DFMO.

Another preferred type of conjugate has the following structure:

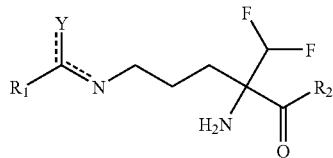

wherein $R_1$ is H, $X_1H$, $X_1R_3$, or $R_3$; $R_2$ is $X_2H$ or $X_2R_4$; each of Y, $X_1$, and $X_2$ is, independently, O, N, or S; and each of $R_3$ and $R_4$ is, independently, $C_{1-30}$ alkyl or $C_{2-30}$ aryl. In some preferred embodiments, Y is O and $R_1$ is $R_3$.

Another preferred type of conjugate has one of the following structures:

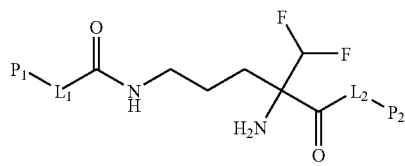

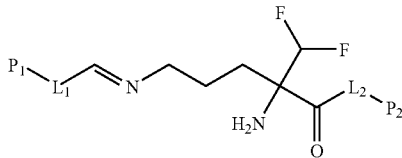

wherein each of $P_1$ and $P_2$, independently, is a natural or synthetic polymer; and each of $L_1$ and $L_2$, independently, is $(CH_2)_n$, where n is 0 to 40, or $(CH_2CH_2X)_m$, wherein m is 0 to 100 and X is O, N, or S. In some embodiments, the polymer is selected from the group consisting of celluloses, chitosans, cyclodextrans, mannans, polylysines, poly-aspartic acids, polyglutamic acids, polyserines, polystyrenes, polyvinyls, polyurethanes, polyethyleneglycols, acrylates, acrylamides, and proteins.

"Conjugate" of DFMO, as used herein, means any compound including the backbone of the DFMO molecule, specifically:

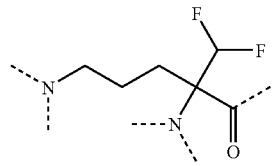

"Alkyl", as used herein, includes alkyl groups that are straight chained or branched, saturated or unsaturated, acylic or cyclic (for example, mono, bi, or tricyclic), and unsubstituted or substituted (for example, alkanols, alkanethiols, alkylamines, and alkylhalides). The carbon chain in the alkyl group may include one or more heteroatoms. Similarly, "aryl" as used herein, includes aryl groups that are unsubstituted or substituted (for example, with alkyl or halogen) and may include one or more heteroatoms.

The present invention also provides conjugates of DFMO or pharmaceutically acceptable salts thereof.

The present invention also provides topical compositions including a dermatologically or cosmetically acceptable vehicle and a conjugate of DFMO or pharmaceutically acceptable salt thereof. The composition may include, for example, from about 0.1% to about 20%, and preferably from about 5% to about 15%, of the conjugate by weight.

Other features and advantages of the invention will be apparent from the detailed description and from the claims.

BRIEF DESCRIPTION OF THE FIGURE

The FIGURE is a plot of percent skin penetration of applied dose (y axis) versus time in hours (x axis).

DETAILED DESCRIPTION

The preferred composition includes a conjugate of DFMO in a cosmetically and/or dermatologically acceptable vehicle. When the conjugate is a Schiff base, the vehicle preferably is non-aqueous. Generally, the composition may be a solid, semi-solid, cream, or liquid. The composition may be, for example, a cosmetic and dermatologic product in the form of, for example, an ointment, lotion, foam, cream, gel, or solution. The composition may also be in the form of a shaving preparation or an aftershave. The vehicle itself can be inert or it can possess cosmetic, physiological and/or pharmaceutical benefits of its own.

The composition may include one or more other types of hair growth reducing agents, such as those described in U.S. Pat. No. 5,364,885 or U.S. Pat. No. 5,652,273. The composition may also include, for example, non-conjugated DFMO. In addition, the entity used to form the conjugate with DFMO may itself have hair growth reducing properties.

applied is limited-only by the rate at which the conjugate penetrates the skin. The effective amounts may range, for example, from 10 to 3000 micrograms or more per square centimeter of skin.

Vehicles can be formulated with liquid or solid emollients, solvents, thickeners, humectants and/or powders. Emollients include, for example, stearyl alcohol, mink oil, cetyl alcohol, oleyl alcohol, isopropyl laurate, polyethylene glycol, olive oil, petroleum jelly, palmitic acid, oleic acid, and myristyl myristate. Solvents include, for example, water (except when the conjugate is a Schiff base), ethyl alcohol, isopropanol, acetone, diethylene glycol, ethylene glycol, dimethyl sulfoxide, and dimethyl formamide.

The conjugates may be synthesized according to known general procedures. For example, when the conjugate is a Schiff base, ester, carbamate, carbamide, or amide of DFMO, the following synthetic pathways can be used to synthesize the conjugate:

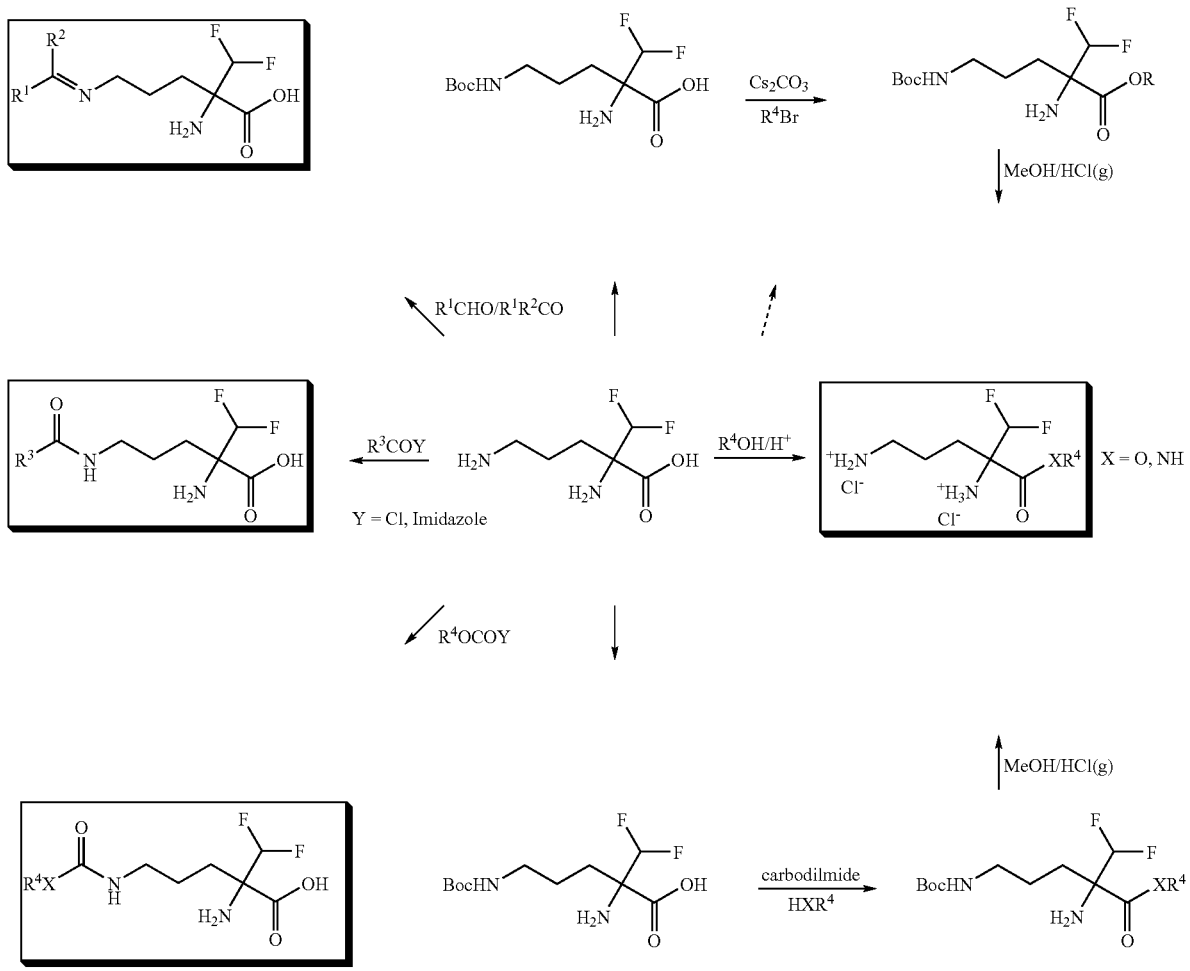

The concentration of the conjugate in the composition may be varied over a wide range, preferably from 0.1% to 30% by weight; the reduction of hair growth generally increases as the amount of the conjugate applied increases per unit area of skin. The maximum amount effectively In the above pathway, the Schiff bases are obtained using aldehydes ($R^1CHO$ above) or ketones ($R^1R^2CO$ above); the amides are obtained using amine ($HXR^4$, above, where X is NH); the carbamides are obtained using carboxylic acids (which are converted to $R^3COY$ above); and the carbamates and esters are obtained using alcohols (R⁴OH or alcohols converted to R⁴OCOY, above). Examples of aldehydes, ketones, carboxylic acids, and alcohols that can be used are provided in Table 1.

conditions or by terminating the reaction at an appropriate time. The ionization constants of DFMO have been determined utilizing potentiometric titration. Three constants were obtained: $pK_1=0.084$, $pK_2=6.437$, $pK_3=10.393$. Mono-

TABLE 1

|  | Aldehydes | Ketones | Acids | Alcohols |
|---|---|---|---|---|
| Acyclic | C1-40 alkanal | C1-40 alkanone | C1-40 alkanoic Acid | C1-40 alkanol |
|  | C3-40 Isoalkanal | C3-40 isoalkanone | C3-40 Isoalkanoic Acid | C3-40 Isoalkanol |
|  | C1-40 alkenal | C1-40 alkenone | C1-40 alkenoic Acid | C1-40 alkenol |
|  | lauraldehyde | acetone | gamma-linolenic acid | citronellol |
|  | crotonaldehyde | methyl ethyl ketone | myristic acid | methanol |
|  | capric aldehyde | stearone | oleic acid | butanol |
|  | decyl aldehyde | methyl isobutyl ketone | n-(phosphonoacetyl)-L-aspartate | geranylgeraniol |
|  | isovaleraldehyde | palmityl trifluoromethyl ketone | s-methylglutathione | d-pantothenic acid |
|  | undecylenic aldehyde | arachidonyl trifluoromethyl ketone | 2,3-diaminoproprionic acid | hexylene glycol |
|  | caproic aldehyde |  | 1-canavanine | farnesol |
| Cyclic | perillaldehyde | camphor | cholic acid | menthol |
|  | furaldehyde | carvone | ursodeoxycholic acid | borneol |
|  | retinaldehyde | 2-heptylcyclopentanone | fusidic acid | retinol |
|  | 2,4-dimethyl-3-cyclohexene carboxaldehyde | isopentylcyclohexanone | (S)-(−)-2-pyrrolidone-5-carboxylic Acid | triamcinolone acetonide |
|  |  | spironolactone | oleanolic acid | prednisolone |
|  |  | progesterone | chlorogenic acid | dexamethasone |
|  |  | cyproterone | L-mimosine | cholesterol |
|  |  |  | betulinic acid | 17-α-testosterone |
|  |  |  | simvastatin acid | Fluocinolone |
|  |  |  | carbenoxolone | 17α-allyltestosterone |
|  |  |  | 3-oxo-4-androsten-17β-carboxylic acid | 17α-propyltestosterone |
|  |  |  |  | perillyl alcohol |
| Aromatic | anisaldehyde | p-methyl acetophenone | ferulic acid | phenylisohexanol |
|  | 2-(phenylmethylene) heptanal | 4-(4-hydroxyphenyl)-2-butanone | 3,4-dimethoxycinnamic acid | amylcinnamyl alcohol |
|  | 4-t-butyl benzaldehyde | phloridzin | 3,4-dihydroxycinnamic acid | phenylpropanol |
|  | alpha-amylcinnamaldehyde | nabumetone | nalidixic acid | cinnamyl alcohol |
|  | amyl cinnamic aldehyde |  | thiosalicylic acid | phenethyl alcohol |
|  | benzaldehyde |  | trimesic acid | phenoxyethanol |
|  | pyridoxal phosphate |  | mycophenolic acid | benzyl alcohol |
|  | amyl cinnamic aldehyde |  | naproxen | genistein |
|  | piperonal |  | ketoprofen | fisetin |
|  | cinnamaldehyde |  | fluvastatin | apigenin |

The synthetic transformation procedures and kinetics giving rise to Schiff base, ester, carbamate or carbamide has been well documented. Detailed references can be obtained, for example, from the following sources;

1. Jerry March, Advanced Organic Chemistry, 4$^{th}$ edition, John Wiley & Sons; July 1992.
2. S. Patai, The Chemistry of the Carbon Nitrogen Double Bond, Wiley, 1970.
3. Comprehensive Organic Transformations: A Guide to Functional Group Preparations, 2$^{nd}$ Edition. Richard C. Larock, November 1999.

Conjugates including DFMO bonded to a natural or synthetic polymer, optionally through a linker, can be prepared using known procedures. Commercially available (for example, from Apollo Scientific Ltd, Cheshire, UK, EMD Biosciences, Inc., USA, Molecular Probes, Inc., USA) homo- and heterobifunctional linkers can be used in the well-established prior art of linking biomolecules or polymers with smaller functional molecules. Bifunctional linkers couple to macromolecules through reactive termini, specific for nucleophilic moieties on the polymer or biopolymer and small functional molecule.

Schiff Base Formation:

Although Schiff base formation is possible at both amino groups, sufficient selectivity can be achieved under buffered conditions or by terminating the reaction at an appropriate time. The ionization constants of DFMO have been determined utilizing potentiometric titration. Three constants were obtained: $pK_1=0.084$, $pK_2=6.437$, $pK_3=10.393$. Mono-conjugated Schiff base was prepared by reaction with a selected aldehyde or ketone under controlled buffer conditions. For skin penetration studies, $^{14}$C-DFMO was added to the non radiolabeled DFMO solution. The formation of the Schiff base was demonstrated by an increase in absorbance at 390 nm.

Synthesis of DFMO-benzaldehyde Schiff Base.

DFMO was dissolved in water at 30% (w/w), followed by adjusting the pH from 3.7 to 8.0 using concentrated NaOH. DFMO for Schiff base preparation was isolated from an aqueous solution at pH 8 by lyophilization or ethanol precipitation. For skin penetration studies, $^{14}$C-DFMO was added to the DFMO solution prior to ethanol addition. The derived DFMO salt was added to the desired vehicle containing the benzaldehyde. The final mixture contained 1% (w/w) DFMO and up to a 5-fold molar excess of benzaldehyde over unconjugated DFMO. The reaction mixture was shaken for 18-96 hours using Orbitron Rotator I (Boekel Scientific) until clear solution was obtained. The formation of the Schiff base was characterized by an increase in absorbance at 390 nm. The Schiff base prepared was used in skin permeation studies.

The DFMO Schiff base was also synthesized using microwave chemistry. A 1.5-fold molar excess of DFMO (unmodified free acid monohydrochloride salt) suspended in neat benzaldehyde (or as a combination with an aprotic polar solvent dimethylformamide or 1-methyl-2-pyrrolidinone) was placed in a sealed wheaton vial, followed by microwave irradiation (6×15 sec). In order to avoid a huge pressure build-up, the vial pressure was released between heating cycles. Excess DFMO was removed by partitioning the crude product mixture between ethyl acetate and brine. The crude Schiff base was isolated from the organic phase after evaporation under reduced pressure. Further purification was achieved by flash chromatography, using BondElute® silica cartridges and a mixture of ethyl acetate and heptane as eluant. The resulting DFMO-benzaldehyde Schiff base was characterized by GCMS, as the $M^+$—$CO_2$—HF—$NH_3$.

The other Schiff bases of DFMO listed in Table 2 (first six compounds listed) were prepared in a similar manner. Other aldehydes and ketones listed in Table 1 also can be used to form a Schiff base of DFMO in a similar manner.

Ester, Carbamide and Carbamate Formation:

In order to synthesize DFMO esters, the α- and δ-amino groups with an acid labile protecting group in order to prevent self-condensation. Due to steric hinderance at the α-carbon, only the δ-amino tertiary-butyloxycarbonyl (t-Boc) protected DFMO product was isolated. Hence, all DFMO-carbamates or carbamides were regioselectively coupled at the 6-amino group. DFMO esters have been synthesized from t-Boc-DFMO-OH utilizing $CsCO_3$ mediated O-alkylation followed by methanolic HCl deprotection of the t-Boc-ester. The original DFMO synthetic procedure used by Bey et al was used to synthesize $^{14}C$-DFMO-Ome for skin permeation studies (see Bey et al *J. Org. Chem.*, 44, 1979, 2732-2742).

Synthesis of t-Boc-DFMO-OH (a DFMO Carbamate)

A 100 mL, round-bottomed flask, equipped with an efficient stirrer, a dropping funnel was charged with a solution of 20 mL of NaOH (1N). Stirring was initiated and 2.36 g (10 mmol) of DFMO was added at ambient temperature, and then diluted with 15 mL of tert-butyl alcohol. To the well-stirred, clear solution was added dropwise within 1 hr, 4.46 g (20.4 mmol) of di-tert-butyl dicarbonate. The reaction was allowed to stir overnight at room temperature. The reaction mixture was extracted with heptane (3×5 ml). The product remains in the aqueous phase, which was acidified (pH 2-3) with HCl (1N) in order to decompose any unreacted di-tert-butyl dicarbonate. The mixture was subsequently neutralized with triethylamine. After evaporating excess triethylamine, the aqueous mixture was lyophilized to dryness. The resulting white residue, was dissolved in a mixture of hot water (10%) and triethylamine (1%) in ethanol and applied to a silica gel cartridge (10 g, varian bond elute) followed by elution with the latter solvent system. Fractions containing product were pooled and evaporated to dryness, to give product t-Boc-DFMO-OH (4 g, 149% as free base and acid or 95% based on the triethylammonium hydrochloride salt M+137.98)

Synthesis of $N^5$-myristoyl-DFMO

To a solution of myristic acid in dichloromethane (3.5 ml) was added one equivalent of dicyclohexylcarbodiimide. The mixture was allowed to stir at room temperature for 30 min. A suspension of DFMO in dimethylformamide (6 ml) and a catalytic amount (10 mol %) of N,N-dimethylaminopyridine were added to the dichloromethane solution. The resulting suspension was allowed to stir for 18 hrs at room temperature, followed by the evaporation of solvents and resuspension in dichloromethane. The insoluble dicyclohexylurea and unreacted DFMO were filtered and the filtrate was evaporated to give $N^5$-myristoyl-DFMO (ca. 1 g). APCI MS: M+1, 393.1.

Other fatty acids listed in Table 1 can be used to form a DFMO carbamide in a similar manner.

DFMO-methyl Ester Dihydrochloride

Boc-DFMO-OH was dissolved in tetrahydrofuran (2 ml), followed by addition of cesium carbonate (in 1 ml water). The mixture was allowed to stir for 15 min, after which it was evaporated to dryness, followed by 2×2 ml co-evaporations with anhydrous dimethylformamide. The resulting product was suspended in anhydrous dimethylformamide (5 ml), followed by the addition of methyl iodide. The mixture was allowed to stir overnight in a sealed tube. Thin layer chromatography (50% EtAc and heptane) showed the formation of a major product and two minor, less polar products. The reaction was quenched by the addition of 15 ml of saturated aqueous NaCl, followed by extraction with ethyl acetate. Evaporation of the combined organic solvent gave the crude product t-Boc-DFMO-OMe (0.7 g). The crude mixture was purified by chromatography (Varian SPE, silica gel BondElute column 10 g) using 10-20% ethyl acetate in heptane as eluant, to give t-Boc-DFMO-OMe (0.4 g). $^1$H NMR: ($CDCl_3$) 1.4 (9H), 1.6 (6H), 3.1 (2H), 3.8 (3H), 4.6 (1H), and 5.9 (1H). GCMS: M+1, 297.

Acetyl chloride (239 µl) was slowly added to anhydrous methanol (0.5 ml) at 0° C., and stirred for 5 min to ensure complete formation of methanolic HCl and methyl acetate. Boc-DFMO-OMe (249 mg) was prepared in anhydrous methanol and added to the methanolic HCl solution. The reaction mixture was allowed to stir at room temperature for 30 min or until complete t-Boc deprotection (thin layer chromatography, 5:3:1, n-butanol:acetic acid:water). The solvents were evaporated by a steady stream of argon, to give the DFMO-methyl ester dihydrochloride salt. Extraction with diethyl ether removed traces of t-Butyl alcohol. $^1$H NMR: ($D_2O$) 1.7 (1H), 1.9 (1H), 2.2 (2H), 3.0 (2H), 4.0 (3H) and 6.5 (1H).

Other alcohols listed in Table 1 can be used to form DFMO ester in a similar fashion via conversion of the alcohol to the alkylhalide, thiol or homologous amines. These synthetic transformations are known; see, for example, Comprehensive Organic Transformations: A Guide to Functional Group Preparations, $2^{nd}$ Edition. Richard C. Larock, November 1999.

TABLE 2

| DFMO conjugate | Abbreviated CODE |
|---|---|
| 2-amino-5-(benzylidene-amino)-2-difluoromethyl-pentanoic acid | B-DFMO |
| 2-amino-2-difluoromethyl-5-[(4-hydroxy-3-methoxy-benzylidene)-amino]-pentanoic acid | V-DFMO |
| 2-amino-2-difluoromethyl-5-(2-methyl-3-phenyl-allylideneamino)-pentanoic acid | MCA-DFMO |
| 2-amino-2-difluoromethyl-5-[(☐aphthalene-2-ylmethylene)-amino]-pentanoic acid | N-DFMO |
| 2-amino-2-difluoromethyl-5-[(4-isopropyl-benzylidene)-amino]-pentanoic acid | IPB-DFMO |
| 2-amino-2-difluoromethyl-5-[(2,4,6-trimethyl-benzylidene)-amino]-pentanoic acid | M-DFMO |
| 2,5-diamino-2-difluoromethyl-pentanoic acid methyl ester | DFMO-OMe |
| 2-amino-5-tert-butoxycarbonylamino-2-difluoromethyl-pentanoic acid | Boc-DFMO |
| 2-amino-2-difluoromethyl-5-myristoylamino-pentanoic acid | Myr-DFMO |

Compositions including a DFMO conjugate/derivative and a suitable vehicle are provided in Table 3.

TABLE 3

| Abbreviated CODE from Table 2 | Example # | water | Ethanol | PG[a] | DPG[b] | BnOH[c] | PC[d] |
|---|---|---|---|---|---|---|---|
| DFMO[#] | 1 | 68 | 16 | 5 | 5 | 4 | 2 |
| B-DFMO | 2 | 0 | 84 | 5 | 5 | 4 | 2 |
| V-DFMO | 3 | 0 | 84 | 5 | 5 | 4 | 2 |
| MCA-DFMO | 4 | 0 | 84 | 5 | 5 | 4 | 2 |
| N-DFMO | 5 | 0 | 84 | 5 | 5 | 4 | 2 |
| IPB-DFMO | 6 | 0 | 84 | 5 | 5 | 4 | 2 |
| M-DFMO | 7 | 0 | 84 | 5 | 5 | 4 | 2 |
| DFMO-OMe | 8 | 68 | 16 | 5 | 5 | 4 | 2 |
| Boc-DFMO | 9 | 68 | 16 | 5 | 5 | 4 | 2 |
| Myr-DFMO | 10 | 0 | 84 | 5 | 5 | 4 | 2 |

[a]Propylene glycol; dipropylene glycol; Benzyl alcohol; and Propylene carbonate.

Use

The composition should be topically applied to a selected area of the body from which it is desired to reduce hair growth. For example, the composition can be applied to the face, particularly to the beard area of the face, i.e., the cheek, neck, upper lip, or chin. The composition also may be used as an adjunct to other methods of hair removal including shaving, waxing, mechanical epilation, chemical depilation and electrolysis.

The composition can also be applied to the legs, arms, torso or armpits. The composition is particularly suitable for reducing the growth of unwanted hair in women, particularly unwanted facial hair, for example, on the upper lip or chin. The composition should be applied once or twice a day, or even more frequently, to achieve a perceived reduction in hair growth. Perception of reduced hair growth can occur as early as 24 hours or 48 hours (for instance, between normal shaving intervals) following use or can take up to, for example, three months. Reduction in hair growth is demonstrated when, for example, the rate of hair growth is slowed, the need for removal is reduced, the subject perceives less hair on the treated site, or quantitatively, when the weight of hair removed (i.e., hair mass) is reduced (quantitatively), subjects perceive a reduction, for example, in facial hair, or subjects are less concerned or bothered about their unwanted hair (e.g., facial hair).

Penetration Assay of DFMO Conjugates

The penetration studies were carried out using Franz chambers. Hamster skin (non-flank organ region) was clipped and appropriate size pieces then cut and mounted between the lower and upper Franz cell chambers. The lower and upper chambers (with the skin in between) were then securely clamped together. A small magnetic stir bar was placed in the bottom of each chamber, 80 μL of 100× sodium azide to a final concentration of 0.2% was added as an anti-microbial agent, then the lower chamber was filled with phosphate buffered saline (PBS). PBS is added until the level in the side arm is just level with the mounted skin, slightly inverting the cells as necessary to remove any air bubbles that might occur. The Franz chambers are then placed in the appropriate size heating blocks and allowed to stand overnight at room temperature. The following morning, 20 μL of a formulation containing 1% radiolabeled DFMO, as the control, was applied to each skin sample and carefully spread over the skin surface using a glass rod. Similarly, 20-40 μL of a 1% test formulation was applied over 8-10 chambers. Four hundred μL of the receptor fluid from the lower chamber was removed at 2, 4, 6, 8, 24 and 50 hours and placed in a scintillation vial. This PBS was then replaced with 400 μL of fresh PBS. DFMO penetration through the skin was assessed by measurement of radioactivity using liquid scintillation counting.

In vitro Drug Skin Accumulation Assay

After the 50-hour receiver fluid sample was taken, the diffusion set-up was dismantled. The skin section was mounted on a board and the stratum corneum skin layer was removed by tape stripping (3M Magic Tape 810). The section of the remaining skin exposed to the receiver fluid was isolated, placed in a vial containing 1 ml of Beckman Tissue Solubilizer-450, shaken for 4 days, and the resulting solution was assayed for the radiolabeled drug.

Referring to the FIGURE, skin penetration studies of B-DFMO (triangles) and DFMO (circles) were carried out with 9 replicates each. The data from the two studies was averaged and is plotted in the FIGURE. B-DFMO in alcoholic vehicle base resulted in increased enhancement in penetration relative to DFMO. The level of radiolabeled drug in the receptor fluid was 10±1% of the applied dose after 24 hours and 16±3% after 50 hours. For the formulation containing unconjugated DFMO, the difference was negligible over the same time course (compare 2.6±1.7% and 3.5±2.0%, respectively).

The rate of skin penetration for DFMO-OMe was doubled after 24 hours compared to DFMO. See Table 4, below. In addition, the initial rate of penetration of the B-DFMO was increased compared to DFMO, demonstrating improved transdermal kinetics. See Table 5, below. In general, an increase in the lipophilicity of the DFMO conjugate/derivatives resulted in enhanced penetration. See Table 6, below. DFMO conjugates/derivatives that are highly lipophilic accumulate in the skin, thus allowing a slow release of DFMO. See Table 7.

TABLE 4

| | Rate of Penetration | | | Fold Enhancement |
|---|---|---|---|---|
| Formulation | 4 h | 6 h | 24 h | After 24 h |
| DFMO | 0.17 ± 0.11 | 0.14 ± 0.09 | 0.09 ± 0.05 | 1 |
| DFMO-OMe | 0.23 ± 0.18 | 0.21 ± 0.16 | 0.2 ± 0.13 | 2 |

TABLE 5

| | Initial Rate of Penetration | | | Fold Enhancement |
|---|---|---|---|---|
| Formulation | 2 h | 4 h | 6 h | After 6 h |
| DFMO | 0.53 ± 0.33 | 0.86 ± 0.53 | 1.07 ± 0.65 | 1 |
| B-DFMO | 1.24 ± 1.16 | 1.65 ± 1.48 | 1.71 ± 1.50 | 1.6 |

TABLE 6

| DFMO conjugate | DFMO conjugate[#] | Fold increase |
|---|---|---|
| DFMO (free) | 2.62 ± 1.76 | 1.0 |
| B-DFMO | 9.63 ± 1.31 | 3.7 |

TABLE 6-continued

| DFMO conjugate | DFMO conjugate# | Fold increase |
|---|---|---|
| V-DFMO | 3.34 ± 1.97 | 1.3 |
| MCA-DFMO | 3.28 ± 0.88 | 1.3 |
| N-DFMO | 3.91 ± 0.71 | 1.5 |
| IPB-DFMO | 3.31 ± 0.98 | 1.3 |
| M-DFMO | 6.68 ± 1.68 | 2.6 |

% of applied dose after 24 hr

TABLE 7

| DFMO conjugate | % Skin Deposition | Relative Deposition* |
|---|---|---|
| DFMO | 0.80 ± 0.1 | 1.0 |
| V-DFMO | 0.96 ± 0.6 | 1.2 |
| MCA-DFMO | 4.00 ± 3.0 | 5.0 |
| B-DFMO | 5.92 ± 4.0 | 7.4 |

*fold increase over unconjugated DFMO after 50 hr
Other embodiments are within the claims.

What is claimed is:

1. A method of reducing hair growth in a human, comprising selecting an area of skin from which reduced hair growth is desired, and applying to the area of skin, in an amount effective to reduce hair growth, a dermatologically acceptable composition including a conjugate of α-difluoromethylornithine or a pharmaceutically acceptable salt thereof, wherein the conjugate has the structure

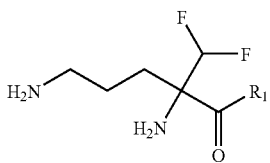

wherein $R_1$ is $XR_2$; X is O, N, or S; and $R_2$ is H, $C_{1-30}$ alkyl, or $C_{2-30}$ aryl; except that, when X is O, $R_2$ is not H.

2. The method of claim 1, wherein X is O.

3. The method of claim 2, wherein the compound is selected from the group consisting of 2,5-diamino-2-difluoromethyl-pentanoic acid 3,7-dimethyl-oct-6-enyl ester; 2,5-diamino-2-difluoromethyl-pentanoic acid 1-(2,6-dimethyl-hepta-1,5-dienyl)-4,8-dimethyl-nona-3,7-dienyl ester; 2,5-diamino-2-difluoromethyl-pentanoic acid 3-(2-carboxy-ethylcarbamoyl)-3-hydroxy-2,2-dimethyl-propyl ester; 2,5-diamino-2-difluoromethyl-pentanoic acid 6-hydroxy-hexyl ester; 2,5-diamino-2-difluoromethyl-pentanoic acid 6-(2,5-diamino-2-difluoromethyl-pentanoyloxy)-hexyl ester; 2,5-diamino-2-difluoromethyl-pentanoic acid 3,7,11-trimethyl-dodeca-2,6,10-trienyl ester; 2,5-diamino-2-difluoromethyl-pentanoic acid 2-isopropyl-5-methyl-cyclohexyl ester; 2,5-diamino-2-difluoromethyl-pentanoic acid 1,7,7-trimethyl-bicyclo[2,2,1]hept-2-yl ester; 2,5-diamino-2-difluoromethyl-pentanoic acid 3,7-dimethyl-9-(2,6,6-trimethyl-cyclohex-1-enyl)-nona-2,4,6,8-tetraenyl ester; 2,5-diamino-2-difluoromethyl-pentanoic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester; 2,5-diamino-2-difluoromethyl-pentanoic acid 2-(11,17-dihydroxy-10,13-dimethyl-3-oxo-6,7,8,9,10,11,12,13,14,15,16,17-dodecahydro-3H-cyclopenta[a]phenanthren-17-yl)-2-oxo-ethyl ester; 2,5-diamino-2-difluoromethyl-pentanoic acid 10,13-dimethyl-3-oxo-2,3,6,7,8,9,10,11,12,13,14,15,16,17-tetradecahydro-1H-cyclopenta[a]phenanthren-17-yl ester; 2,5-diamino-2-difluoromethyl-pentanoic acid 4-isopropenyl-cyclohex-1-enylmethyl ester; 2,5-diamino-2-difluoromethyl-pentanoic acid 4-methyl-1-phenyl-pentyl ester; 2,5-diamino-2-difluoromethyl-pentanoic acid 1-pentyl-3-phenyl-allyl ester; 2,5-diamino-2-difluoromethyl-pentanoic acid 3-phenyl-propyl ester; 2,5-diamino-2-difluoromethyl-pentanoic acid phenethyl ester; 2,5-diamino-2-difluoromethyl-pentanoic acid 2-phenoxy-ethyl ester; 2,5-diamino-2-difluoromethyl-pentanoic acid 17-allyl-10,13-dimethyl-3-oxo-2,3,6,7,8,9,10,11,12,13,14,15,16,17-tetradecahydro-1H-cyclopenta[a]phenanthren-17-yl ester; 2,5-diamino-2-difluoromethyl-pentanoic acid 10,13-dimethyl-3-oxo-17-propyl-2,3,6,7,8,9,10,11,12,13,14,15,16,17-tetradecahydro-1H-cyclopenta[a]phenanthren-17-yl ester 2,5-diamino-2-difluoromethyl-pentanoic acid benzyl ester or 2,5-diamino-2-difluoromethyl-pentanoic acid 4-(5,7-dihydroxy-4-oxo-4H-chromen-3-yl)-phenyl ester.

4. The method of claim 2, wherein $R_2$ is methyl, propyl or butyl.

* * * * *